US005653998A

United States Patent [19]
Hamann et al.

[11] Patent Number: 5,653,998
[45] Date of Patent: Aug. 5, 1997

[54] INJECTABLE LIPOSOMAL PHARMACEUTICAL PREPARATIONS

[75] Inventors: Hans-Jürgen Hamann, Dormagen; Peter Serno, Bergisch Gladbach; Matthias Herboth, Leverkusen; Peter Kurka, Hilden, all of Germany

[73] Assignee: Bayer Aktiengesellschaft, Leverkusen, Germany

[21] Appl. No.: 523,662

[22] Filed: Sep. 5, 1995

[30] Foreign Application Priority Data

Sep. 12, 1994 [DE] Germany .......... 44 32 378.6

[51] Int. Cl.$^6$ .......... A61K 9/127
[52] U.S. Cl. .......... 424/450
[58] Field of Search .......... 424/450; 428/402.2

[56] References Cited

U.S. PATENT DOCUMENTS

| | | | |
|---|---|---|---|
| 4,976,964 | 12/1990 | Schlossman | 424/450 |
| 5,225,558 | 7/1993 | Stoltefuss et al. | 546/167 |
| 5,380,851 | 1/1995 | Stoltefuss et al. | 546/167 |
| 5,432,282 | 7/1995 | Stoltefuss et al. | 546/167 |

FOREIGN PATENT DOCUMENTS

| | | |
|---|---|---|
| 0200068 | 11/1986 | European Pat. Off. . |
| 0560138 | 9/1993 | European Pat. Off. . |

OTHER PUBLICATIONS

M.K. Jain, et al., J. Membrane Biol., vol. 34, pp. 157–201, (1977).

N. Muranushi, et al., International Journal of Pharmaceutics, vol. 4, pp. 281–290, (1980).

J.H. Crowe, et al., Database Medline, AN: 89134809, abstract of Biochim. Biophys. Acta., vol. 979, No. 1, pp. 7–10, (1989).

G.V. Betageri, et al., "Liposome Drug Delivery Systems", pp. 118–119, Technomic Publishing Co. Inc., Lancaster, PA. (1993).

Y. Ozer, et al., Acta. Pharm. Technol., vol. 34, (3), pp. 129–139, (1988).

J.H. Crowe, et al., Biochimica et Biophysica Acta, vol. 979, pp. 7–10, (1989).

*Primary Examiner*—Gollamudi S. Kishore
*Attorney, Agent, or Firm*—Sprung Horn Kramer & Woods

[57] ABSTRACT

The invention relates to stable liposomal injectable formulations for lipophilic, poorly soluble active compounds, in the form of liposomes which are stabilized by short-chain fatty acids, in particular for active compounds from the dihydropyridines group.

8 Claims, No Drawings

INJECTABLE LIPOSOMAL PHARMACEUTICAL PREPARATIONS

The invention relates to stable liposomal injectable formulations for lipophilic, poorly soluble active compounds, in the form of liposomes which are stabilized by short-chain fatty acids, in particular for active compounds from the dihydropyridines group.

Intravenously administrable formulations are needed for many useful pharmaceutical active compounds, e.g. for a rapid initial therapy, for acute emergency situations and also for the treatment of severe clinical cases. Many active compounds, including many dihydropyridines, have a very poor water solubility and thus cannot be formulated in aqueous solution. A further problem is the sensitivity to hydrolysis and oxidation of many substances.

The problem of the solubility and the sensitivity to hydrolysis can be solved by the use of customary organic solvents, such as ethanol, polyethylene glycol or propylene glycol. Many of these solvents, however, have a poor local tolerability and must therefore be administered via a central catheter or diluted with aqueous infusion solutions. As a result of poor water solubility, the latter can lead to supersaturation and to occurrence of crystallization. In the case of relatively long intravenous therapy, the amounts of organic solvents to be administered here are often toxicologically unacceptable. The use of solubilizing soap or surfactant micelles, which can be formulated by incorporating the active compound in aqueous sodium lauryl sulphate or polysorbate solutions, is likewise problematical, as by this means severe complications, such as e.g. haemolysis or shock-like symptoms, can be produced.

Numerous processes are known to incorporate the poorly soluble active compounds in nanoparticulate excipients and in this way substantially to dispense with the use of toxic solvents and surfactants. These include e.g. the parenteral emulsions, lecithin-bile salt mixed micelles and liposomes. In these systems the active compounds are present as colloidal particles in water, so only active compounds which are stable to hydrolysis can be incorporated.

It is likewise known that liposomes with the active compounds incorporated therein can be stabilized by freeze-drying (cf. Betageri et al., Liposome Drug Delivery Systems, Technomic Publishing AG Basel, 1993, page 118). To do this, the addition of a cryoprotector is necessary, which, as a result of its membrane-stabilizing action, guarantees the integrity of the liposomes. Known cryoprotectors are polyalcohols such as e.g. glycerol, monosaccharides such as glucose, disaccharides such as e.g. sucrose, lactose or trehalose and proteins or amino acids (cf. Y. Ötzer et al., Influence of Freezing and Freeze-drying on the Stability of Liposomes Dispersed in Aqueous Media, Acta Pharm. Technol., 34 (3), 1988, pp. 129–139).

Stable, freeze-dried liposomal preparations containing dihydropyridines, e.g. containing nimodipine, have already been disclosed in EP-A-560 138. Preparation there is carried out using phospholipids, customary cryoprotectors and a pH stabilizer.

It appears, however, that certain problematical active compounds, which are both poorly water-soluble and also sensitive to hydrolysis and oxidation, cannot be converted into adequately stable liposome formulations by the methods known hitherto. This applies in particular to dihydropyridines as Nimodipine or those of the general formula (I)

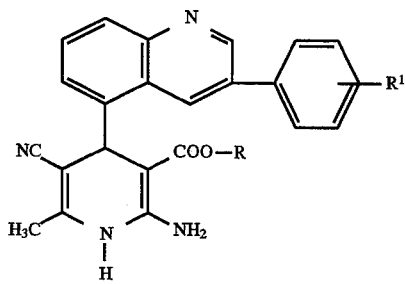

in which

R represents alkyl having 1–6 carbon atoms and

R¹ represents hydrogen, halogen, cyano, difluoromethyl, or alkyl or alkoxy each having 1–4 carbon atoms.

Particularly suitable dihydropyridines are Nimodipine or those of the general formula I for the liposomes according to the invention are those in which R represents alkyl having 1–4 C atoms, in particular n-propyl or isopropyl, and R¹ represents hydrogen, fluorine, chlorine, cyano or trifluoromethyl, in particular hydrogen.

These dihydropyridines are prepared by customary methods, e.g. by the processes described in German Offenlegungsschrift 4 117 750.

The dihydropyridines are highly active medicaments which can be employed, inter alia, for the therapy of cardiac muscle insufficiency. For this indication a stable and rapidly acting i.v. formulation is of particular interest.

The invention thus relates to parenterally administrable stable pharmaceutical preparations based on liposomes having phospholipid membranes, characterized in that, as stabilizer against flocculation, they contain a short-chain fatty acid of the formula II $$H_3C-(CH_2)_n-COOA \qquad (II)$$

in which n represents 4–8, in particular 6, and

A represents hydrogen or a 1- or 2-valent cation, in particular sodium or potassium, the weight ratio of active compound to phospholipid being 1 to 20–200 and the weight ratio of short-chain fatty acid to phospholipid being 1 to 2–60.

Of particular interest are liposomal preparations in which the weight ratio of short-chain fatty acid to phospholipid is 1 to 4–50.

In the attempt to convert dihydropyridine active compounds of the general formula I according to EP-A-560 138 into liposomes, it appears that these were not adequately stable both chemically and physically (see comparison example from A). After short-term storage of only 2 weeks at room temperature, the total amount of undesired breakdown products was no longer tolerable. In addition, marked flocculation and aggregation was seen after reconstitution of the liposomes with distilled water.

Surprisingly, it has been found that chemically and physically stable liposomes can also be obtained with the problematic dihydropyridines of the general formula I if short-chain fatty acids of the general formula II or their salts are added to the liposomes.

The effect, that the liposomes according to the invention have a higher physical stability as a result of addition of short-chain fatty acids or their salts and the undesired flocculation and aggregation after reconstitution is prevented, could not be expected with knowledge of the prior art. In the literature (cf. J. H. Crowe et al., Effects of Free Fatty Acids and Transition Temperature on the Stability of Dry Liposomes, Biochemica et Biophysica Acta, 979, (1989) pp. 7–10), it is reported that customary fatty acids have a membrane-destabilizing and fusogenic effect, i.e. promoting the combination of liposomes. By means of microscopic examinations, gel chromatography and laser correlation spectroscopy, it can be shown that the addition of medium-chain fatty acids in the range of the concentration according to the invention does not significantly affect the particle size of the liposomes, prevents flocculation and aggregation of the liposomes and causes no destabilization. At the same time, it could be shown that the dihydropyridine active compounds are completely (100%) incorporated in the liposomes.

The concentration according to the invention of the short-chain fatty acids is 0.4 to 10 mg per ml of the ready-to-administer liposome dispersion. Based on the amount of the phospholipid employed, one part by weight of the short-chain fatty acid or its salts is employed with 2 to 60, preferably 4 to 50, parts by weight of phospholipid.

The addition of further auxiliaries, in particular of disaccharides such as trehalose, sucrose and lactose, as cryoprotectors is advantageous. Sucrose, in particular, has an optimum cryoprotective action. The cryoprotector-phospholipid ratio is 0.8–4 to 1, preferably 1.2–2.5 to 1.

The active compound-phospholipid ratio is 1 to 20–200, preferably 1 to 30–80, in particular, 1 to 30–50.

To obtain an isotonic pressure, one or more suitable osmotically active agents can also be added to the reconstitution medium. Those which prove suitable are glycerol, mannitol and glucose; in particular glycerol.

If necessary, the liposomes according to the invention can contain further auxiliaries, such as, for example, stabilizers such as antioxidants of the type butylhydroxyanisole, butylhydroxytoluene, alpha-tocopherol and its salts and ascorbic acid and its salts and esters, preferably ascorbic acid and its salts, and also pH-regulating agents such as buffers, acids or bases, in particular ascorbic acid and sodium hydroxide.

According to the invention, customary phospholipids can be employed. Preferably, phospholipids are used which are outwardly uncharged phosphoglycerides which are optionally intramolecular zwitterions and correspond to the general formula III

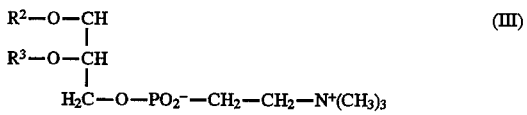

in which $R^2$ and $R^3$ are identical or different and each represents saturated or unsaturated acyl groups having 8 to 24 C atoms, which can optionally be branched and/or substituted.

In addition to the phospholipids of the formula III, phospholipids of a different type such as phosphatidylethanolamines, phosphatidylinositols, sphingomyelins, phosphatidylglycerols and/or phosphatidic acids can also be obtained in smaller amounts. The phospholipids employed can be prepared by purification from natural sources such as soya or crude egg lecithin or synthetically. Purified egg lecithins are preferably employed.

The liposomes according to the invention can be obtained by customary preparation processes, for example by high-pressure homogenization, pore extrusion, dialysis and dilution processes and ultrasonic dispersion, preferably by high-pressure homogenization, such as, for example, microfluidization.

The invention thus also relates to processes for the preparation of the liposomes according to the invention, characterized in that one part by weight of the lipophilic active compound and 20 to 200 parts by weight of phospholipid are predispersed, optionally together with an antioxidant, at a temperature between 10° and 90° C., preferably between 50° and 80° C., in water using a stirrer, optionally with nitrogen gassing, and then homogenized in a high-pressure jet homogenizer at temperatures between 20° and 80° C. and a pressure between 400 and 1500 bar to a mean particle size of 35 to 200 nm and then a cryoprotector and a short-chain fatty acid of the general formula II or its salt are dissolved in a fatty acid phospholipid ratio of 1 to 2–60 in the homogenizate and the dispersion thus obtained is freeze-dried.

In a variant of this process, the active compound and/or the cryoprotector can also be added even during the predispersion or the high-pressure jet homogenization. Likewise, the short-chain fatty acids can also be added to the reconstitution medium so that they only come directly into contact with the liposomes during the reconstitution process. In both cases, flocculation of the reconstituted liposomes is prevented for more than 24 hours, and at the same time the mean particle diameter of the liposomes is retained and the chemical stability of the active compound guaranteed.

On exceeding a concentration of the fatty acids of 10 mg/ml, a destabilization of the liposomes and an escape of the active compound from the liposomes occurs, as can be seen from Comparison Example B. Without the addition according to the invention of short-chain fatty acids, the dispersions flocculate within 24 hours, as can be seen from Comparison Example C.

Exemplary embodiments show for typical active compounds the advantages of the process according to the invention and the stability of the liposomes thus obtained. The Comparison Examples A–C, on the other hand show the instability and the disadvantages of the products which were prepared by processes known hitherto, or which are outside the claimed formulations. All percentage data are percentages by weight.

EXEMPLARY EMBODIMENTS

Exemplary Embodiment 1

5.5997 kg of dist. water are gassed with nitrogen for 30 min. After the gassing, 16.2 g of sodium ascorbate are dissolved in the water and 580.5 g of purified egg lecithin (phosphatidylcholine>94%) are then added. This mixture is dispersed at 65° C. for 30 mixing a high-speed stirrer. After replacement of the evaporated water, the predispersion is filtered through a membrane filter (pore size 8 μm) and transferred to a high-pressure homogenizer.

The dispersion is homogenized by subjecting it to 5 passages at 800 bar and 65° C. After this, 145 g of the active compound isopropyl 2-amino-1,4-dihydro-5-cyano-6-methyl-4-(3-phenylquinoline-5-yl)pyridine-3-carboxylate are added and uniformly distributed in the dispersion at low pressure (25 bar). The mixture is then homogenized by subjecting it to 20 passages at 65° C. and 800 bar. The liposomes are cooled to room temperature.

168.2 mg of sucrose and 0.11 mg of ascorbic acid are added and dissolved per gram of homogenizate yield. The dispersion is adjusted to pH 6.5 using 0.1N NaOH solution and sterile-filtered through a membrane filter (0.2 μm pore size), filled into brown glass vials to 2.5 ml each and freeze-dried.

The average liposome size before freeze-drying is 48 nm. After reconstitution with 10 ml of an aqueous solution containing 0.0495% sodium caprylate and 1.51% glycerol, the mean liposome size is 57 nm. After a standing time of the reconstituted solution of 24 hours, the average liposome size is 57 nm. No flocculation and/or precipitate formation occurs in the reconstituted dispersion within 24 hours. Gel-chromatography examinations show that the active compound is incorporated in the liposomes to 100%.

Exemplary Embodiment 2

1.8561 g of sodium ascorbate is dissolved in 638.33 g of dist. water which has previously been gassed with nitrogen for 10 min. 66 g of purified egg lecithin (phosphatidylcholine content>94%) are added to this solution. The mixture is dispersed at 60° C. for 30 min using a high-speed stirrer. The mixture is then made up to 706.2 g with nitrogen-gassed water and 1.65 g of the active compound according to exemplary embodiment 1 is added. In order to distribute the active compound uniformly, the mixture is dispersed for a further 3 min.

The dispersion is transferred to a high-pressure homogenizer and homogenized at 60° C. and 800 bar for 25 passages.

637.19 g of sucrose are then dissolved in the liposome dispersion and the pH of the dispersion is adjusted to 6.5 using 0.1N NaOH solution.

After sterile filtration (membrane filter 0.2 µm pore size), the finished dispersion is filled into brown glass vials to 2.64 g each and freeze-dried.

After storage of the freeze-dried liposomes at 40° C. for three months, the active compound content is 98.5% and there is no flocculation and/or precipitate within 24 hours after reconstitution with 10 ml of an aqueous solution containing 0.0495 sodium caprylate and 1.51% glycerol.

Exemplary Embodiment 3

12.53 g ascorbic acid and 2.85 g sodium hydroxide are dissolved in 4868.18 g water p.i. under agitation. 504.8 g purified egg lecithin (>94% phospatidylcholine) is added and dispersed with a high-shear mixer.

The dispersion is filtered through a membrane filter (effective maximum pore size 8 µm) and then homogenized in a high-pressure homogenizer (800 bar, 25 cycles).

908.70 g of sucrose is dissolved in the homogenate under agitation. pH adjustment to 6.5 is done by dissolving 0.6 g ascorbic acid and titrating with 0.1N sodium hydroxide solution. The pH adjustment requires approximately 0.1516 g sodium hydroxide. The whole procedure is done under nitrogen blanketing to protect against oxidation.

12.6 g of (4R)isopropyl-2-methoxyethyl 4-(2-chlor-3-cyano-phenyl)-1,4-dihydro-2,6-dimethyl-pyridine-3,5-dicarboxylate is added and the dispersion is stirred for about 12 hours until all of the active compound is dissolved.

The dispersion is filtered again and 11.88 ml (+0.24 ml over-filling) is freeze-dried in 50 ml vials.

The lyophilized product is reconstituted with a solution of 0.725 g glycerine and 0.02375 g sodium caprylate in 47.184 g distilled water.

Exemplary Embodiment 4

4.6583 of dist. water are purged with nitrogen for 10 min. After purging 5.7 g of ascorbic acid and 852.8 g glucose are dissolved in the water. The solution is adjusted to pH 6.5 using 66 g of 0.5M arginine solution. Then 9.502 g of the active compound Nimodipine (isopropyl(2-methoxyethyl)-1,4-dihydro-2,6-dimethyl-4-(3-nitrophneyl)-3,5-pyridine) and 473.8 g of purified egg yolk lecithin (>80% phosphatidylecholine) are added. This mixture is dispersed at 75° C. for 60 min, under nitrogen gassing using a high-speed stirrer. The dispersion is filtered (5 µm pore size) and then transferred to a high-pressure homogenizer.

The dispersion is homogenized for 180 min (60 l/h) at 800 bar and 75° C. The homogenate is cooled below 30° C.

The dispersion is sterile-filtered through a membrane filter (0.2 gm pore size), filled into brown glass vials to 15.30 ml each and freeze-dried.

The liposomes are reconstituted with a solution of 0.0495% sodium caprylate and 1.513% glycerine in water for injection. No flocculation and/or precipitate formation occurs in the reconstituted dispersion for at least 24 hours.

Exemplary Embodiment 5

171.6 of dist. water are purged with nitrogen for 20 min. After purging 200 mg of sodium ascorbate are dissolved in the water, and then 10.0 g of purified egg yolk lecithin (>94%) phosphatidylecholine) and 200 mg of the active compound Etomidat ((R)-ethyl-(α-methylbenzyl)-5-imidazolcarboxylate) are added.

The mixture is dispersed at 60° C. for 20 min, under nitrogen gassing using a high-speed stirrer. After replacement of the evaporated water the predispersion is transferred to a high-pressure homogenizer.

The dispersion is homogenized by subjecting it to 25 passages at 800 bar and 60° C.

After homogenisation, 98.9 mg of sucrose and 1.8 mg sodium caprylate per gram homogenate are added and dissolved. The dispersion is adjusted to pH 6.5 using 1N NaOH solution and sterile-filtered through a membrane filter (0.2 µm pore size), filled into brown glass vials to 20.0 g each and freeze-dried.

The average liposome size before freeze-drying is 56 nm. After reconstitution with 17.16 g glucose-solution(5%), the mean liposome size is 61 nm. No flocculation and/or precipitate formation occurs in the reconstituted dispersion for at least 4 hours.

Exemplary Embodiment 6

1.4 g sodium ascorbate is dissolved in 425 g oxygen-free distilled water. 50 g purified egg phospholipid (>80% phosphatidylecholine) and 1.5 g Paclitaxel (Taxol) are dispersed in this solution with a vortex mixer at 65° C. for 30 minutes.

The dispersion is high pressure homogenized at 725bar at a temperature of 60° C. for 25 cycles.

To 382.32 g of the homogenized dispersion are added 72 g sucrose and 80 mg ascorbic acid. The pH is adjusted to 6.5 by the addition of 0.1N sodium hydroxide solution. The dispersion is made up to 480 g with water.

The dispersion is filtered, and then 12.32 g dispersion (corresponding to 30 mg Paclitaxel+2.67% overfilling) is filled into 50 ml vials and freeze-dried. The freeze-dried product is reconstituted with 29.7 g of a solution containing 0.725 g glycerine and 0.02375 g sodium caprylate in 47.184 g distilled water. The reconstituted dispersion contains 30 mg of solubilized Paclitaxel per 30 ml.

Comparison Examples
Comparison Example A:
(according to EP-A-560 138)

49.1 g of glucose and 0.345 g of ascorbic acid are dissolved in 253 g of dist. water which has previously been gassed with nitrogen for 10 min. The pH is then adjusted to 6.5 using 3.9 g of 0.5M arginine solution. 27.25 g of purified egg lecithin (phosphatidylcholine content>80%), 0.345 g of the active compound according to Exemplary Embodiment 1 and nitrogen-gassed dist. water are added to this solution up to a total weight of 345 g. The mixture is dispersed at 75° C. for 30 min using a high-speed stirrer. After filtration (membrane filter 5 µm pore size), the dispersion is transferred to a high-pressure homogenizer and homogenized at 800 bar and 75° C. for 25 passages.

The finished liposome dispersion is sterile-filtered (membrane filter 0.2 µm pore size), filled into brown glass vials to 2.1 ml each and freeze-dried.

After storage of the freeze-dried liposomes at 40° C. for two weeks, the active compound content falls to 89.7%.

The average particle diameter of the liposomes after high-pressure homogenization is 45 nm. After reconstitution of the freeze-dried liposomes using 9.5 ml of dist. water, the average liposome diameter is 47 nm. The liposome dispersion flocculates within 24 hours after reconstitution and forms a precipitate.

Comparison Example B:
(too much fatty acid)

The liposomes prepared according to Exemplary Embodiment 1 are reconstituted using 10 ml of an aqueous solution containing 5% sodium caprylate and 1.51% glycerol. The liposomes are destabilized. Only 5.3% of the active compound remains incorporated in liposomes.

Comparison Example C:
(no fatty acid)

The liposomes prepared according to Exemplary Embodiment 1 are reconstituted using 10 ml of an aqueous solution containing 1.51% glycerol. The dispersion flocculates within 24 hours and forms a precipitate.

We claim:

1. Parenterally administrable, stable pharmaceutical preparations for lipophilic, poorly soluble active compounds, in the form of liposomes with phospholipid membranes, the active compound/phospholipid weight ratio being 1 to 20–200 and the average liposome diameter being between 35 and 200 nm, characterized in that they contain, as a stabilizer, a short-chain fatty acid of the general formula II $$H_3C-(CH_2)_n-COOA \quad (II)$$

in which
   n represents 4 to 8 and
   A represents hydrogen or a mono- or divalent cation and the concentration of the short-chain fatty acid in the ready-to-administer solution is between 0.3 and 10.0 mg/ml.

2. Pharmaceutical preparation according to claim 1, the weight ratio of the short-chain fatty acids or their salts to the phospholipid being 1 to 2–60.

3. Pharmaceutical preparation according to claim 1 as active ingredient a dihydropyridine.

4. Pharmaceutical preparation according to claim 1 containing as active compound Nimodipine or a dihydropyridine of the formula I

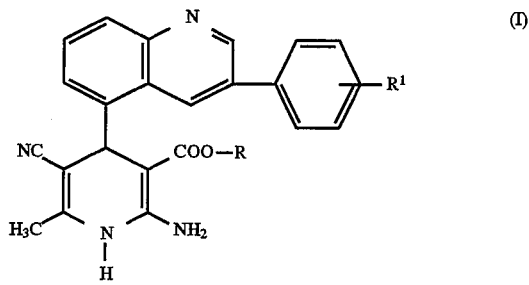

in which

R represents alkyl having 1–6 carbon atoms and $R^1$ represents hydrogen, halogen, cyano, difluoromethyl, or alkyl or alkoxy each having 1–4 carbon atoms.

5. Pharmaceutical preparation according to claim 4 containing as active compound a dihydropyridine of the formula I, in which $R^1$ represents hydrogen, fluorine, chlorine, cyano or trifluoromethyl and R represents alkyl having 1–4 C atoms.

6. Pharmaceutical preparations according to claim 1, characterized in that as cryoprotectors they contain disaccharides.

7. Pharmaceutical preparations according to claim 1, characterized in that as cryoprotectors they contain 0.8 to 4.0 parts by weight of sucrose, relative to one part by weight of phospholipid.

8. A method for stabilizing liposomal preparations of dihydropyridines having phospholipid membranes, which comprises dissolving in said liposomal preparation a short-chain fatty acid of the general formula II $$H_3C-(CH_2)_n-COOA \quad (II)$$

in which n represents 4–8 and

A represents hydrogen or a 1- or 2-valent cation, or a salt thereof.

* * * * *